US006660308B1

(12) United States Patent
Martin et al.

(10) Patent No.: US 6,660,308 B1
(45) Date of Patent: Dec. 9, 2003

(54) BEVERAGE AND ADDITIVE FOR THE ILL

(75) Inventors: Kenneth A. Martin, 8907 Kanis Rd., Suite 330, Little Rock, AR (US) 72205; Teresa Leigh Barr, Port Townsend, WA (US)

(73) Assignee: Kenneth A. Martin, Maumelle, AR (US)

( * ) Notice: Subject to any disclaimer, the term of this patent is extended or adjusted under 35 U.S.C. 154(b) by 0 days.

(21) Appl. No.: 10/241,542

(22) Filed: Sep. 11, 2002

(51) Int. Cl.[7] ................................................ A61K 35/78
(52) U.S. Cl. ........................ 424/728; 514/62; 514/356; 514/709; 426/590
(58) Field of Search ............................ 424/728; 514/62, 514/356, 709; 426/590

(56) References Cited

U.S. PATENT DOCUMENTS

| | | | |
|---|---|---|---|
| 3,686,406 A | * | 8/1972 | Sherlock |
| 4,616,039 A | * | 10/1986 | Herschler |
| 4,621,137 A | * | 11/1986 | Miyake et al. |
| 5,827,834 A | | 10/1998 | Falk |
| 5,852,002 A | | 12/1998 | Falk |
| 5,916,565 A | * | 6/1999 | Rose et al. |
| 5,929,048 A | | 7/1999 | Falk |
| 5,932,560 A | | 8/1999 | Falk |
| 6,194,392 B1 | | 2/2001 | Falk |
| 6,358,526 B1 | * | 3/2002 | Mergens et al. |
| 6,399,093 B1 | | 6/2002 | Petrus |

OTHER PUBLICATIONS

Castleman (The Healing Herbs (1991) Rodale Press; Pennsylvania, pp. 193).*
Derwent abstract of KR 2001018321; Mar. 2001.*

* cited by examiner

Primary Examiner—Leon B. Lankford, Jr.
Assistant Examiner—Susan D. Coe
(74) Attorney, Agent, or Firm—Buskop Law Group, P.C.; Wendy Buskop

(57) ABSTRACT

The invention is a beverage made of a fluid and a one time daily dosage amount in an ingestible amount for treating an inflammatory tissue or arthritic condition in a mammal involving tissue that is underperfused tissue, inflamed joints, and inflamed muscle, wherein said dosage is a rapid absorbing large amount made of a glucosamine sulfate, a glucosamine hydrochloride, and an n-acetyl glucosamine and combinations thereof, a chondroitin sulfate, a chondroitin hydrochloride and combinations thereof, a vasodialating sulfonate with at least one methyl group, and a buffer to reduce adverse symptoms from large amounts of glucosamine and chondroitin selected from the family of araliaceae and a B3 vitamin.

30 Claims, No Drawings

BEVERAGE AND ADDITIVE FOR THE ILL

FIELD OF THE INVENTION

The present invention is a beverage used to treat an inflammatory tissue or arthritic condition in a mammal involving tissue that is underperfused tissue, inflamed joints, or inflamed muscles. The present invention is also a beverage additive in which those who suffer from inflammatory tissues or arthritic conditions can easily receive their daily dosage to ease their pain.

BACKGROUND OF THE INVENTION

A need has existed for a large convenient dosage that is not in a solid form of glucosamine, chondroitin and MSM to be taken in one daily dose that can be quickly absorbed into the bloodstream, thereby bypassing the gut and eliminating the adverse reactions to the elemental ingredients as well as protecting and buffering the lining of the stomach from the high dosages of the ingredients as well as buffering the glucose levels, in the blood, therefore significantly reducing or eliminating the adverse effects of the essential ingredients, and making it possible to administer a one time daily large dose that is fast absorbing, using a powerful vasodilatation system, is tasteless in most liquids, odorless, non- steroidal, has no adverse symptoms of nausea, heartburn, diarrhea, constipation or headache as well as perfusing underperfused tissue by saturating the tissue, increasing mobility of a mammal in all directions, decreasing inflammation, maintain cartilage viability, increase strength, muscle flexibility and endurance that is also cost effective and capable of mass production.

Petrus U.S. Pat. No. 6,399,093 discloses a method and composition for the treatment of musculoskeletal disorders in mammals by the application of a topical composition comprising a permeation enhancing amount of one or more penetration enhancers, and one or more bio-affecting agents to provide anti-inflammatory relief and analgesia to the applied body part.

Falk U.S. Pat. No. 6,194,392 discloses a method of topically applied preparation that relieves pain and includes analgesics using hyaluronic acid in the range of 150,000 to 750,000 daltons where the form of hyaluronic acid is sufficient to provide a dosage greater than 10 mg and less than 3000 mg. Falk U.S. Pat. Nos. 5,827,834; 5,852,002; 5,929, 048; and 5,932,560 refer to methods of using MSM, hyaluronic acid and glucosamine to reduce the swelling of brain tumors in a similar manner as Falk U.S. Pat. No. 6,194,392.

Glucosamine and chondrointin have been touted recently as a supplement for joint and cartilage health. The present invention relates to placing glucosamine and chondrointin in a suspension agent, like corn syrup, high fructose corn syrup, glycerin, glucose, sucrose, can be readily added to juices during manufacture for the mass market and, therefore easy to use and a desirable supplement form for the public.

Some of the chemicals used in this invention are described in the following paragraphs.

Glucosamine, whose scientific name is 2-amino-2-deoxyglucose sulfate, occurs naturally in the human body. Glucosamine provides strength, flexibility, and elasticity to cartilage and connective tissue by stimulating the production of glycosaminoglycans. Glucosamine also decreases inflammation that can lead to joint destruction. Glucosamine is involved in the formation of nails, tendons, skin, eyes, bones, ligaments, and heart valves. More importantly, it contributes to the strength and integrity of joint structures. Connective tissue and cartilage naturally contain high concentrations of glucosamine. When sufficient levels of glucosamine are present, cartilage retains its ability to hold water and act as a shock absorber. Glucosamine sulfate is a simple molecule composed of glucose, an amine, and sulfur. The joints are naturally rich in sulfur molecules, which form important cross-linkages with other molecules. These cross-linkages provide cartilage with its strength, structure, and shock-absorbing qualities. That's one reason glucosamine sulfate is the preferred form of supplemental glucosamine. Another reason is absorbability.

Each person produces a certain amount of glucosamine in his or her bodies. As people age, their bodies no longer produce enough glucosamine causing arthritic conditions such as deformed joints and limited joint movement. Numerous double-blind, placebo controlled, glucosamine studies have been published, all reporting that glucosamine was indeed very effective in treating osteoarthritis and that its use is long-term safe. The studies have also shown that glucosamine provided in liquid form is absorbed more quickly, much more fully, and provides greater and longer lasting relief.

Chondroitin sulfate, whose scientific name is chondroitin 4-sulfate and chondroitin 4- and 6-sulfate, belongs to a class of very large molecules called gycosaminoglycans (GAGs). Chondroitin is manufactured from natural sources, such as shark, bovine and other cartilage extracts and is made up of repeating units of glucosamine with attached sugars. The molecules in these formulas are 250 times larger than glucosamine sulfate. Chondroitin is used for arthritic conditions because it is endogenously found in cartilaginous tissues in most mammals and serves as a substrate for the formation of joint matrix structure. Adverse reactions include epigastric pain, nausea, diarrhea and constipation.

Methylsulfonylmethane (MSM) is a natural form of organic sulfur found in all living organisms. MSM is prevalent throughout the human body. MSM is an important food that plays many roles in the body, including the stimulation of the growth of healthy skin, hair and nails. It is needed by the body for healthy, connective tissues and joint function, proper enzyme activity and hormone balance, along with the proper function of the immune system. MSM is highly soluble in both oil and water. As oxygen is transported from the lungs to the mitochondria, it goes through a number of stages with continually decreasing oxidation potential or effective oxygen concentration. MSM easily and rapidly diffuses through the hydrophilic cell cytoplasm as well as the hydrophobic cell membranes. MSM has no barriers. The human body has no other molecules naturally occurring in our bodies similar to MSM. Oxygen transport is handled by passing it between different molecules that are hydrophilic in the cytoplasm and hydrophobic in the cell membranes.

Hyaluronic acid, also called sodium hyaluronate, or hyaluronan or HA, is a linear polysaccharide composed of repeating disaccharide units of N-acetyl-glucosamine and D-glucuronic acid. The highest concentrations of HA are found in the soft connective tissue where it is a major component of the extra cellular matrix. HA is present in hyaline cartilage, in synovial joint fluid, and in the skin tissue, both dermis and epidermis. Injecting substances with HA into the knee joint provides long-term pain relief for some people with osteoarthritis. Hyaluronic acid is a natural component of cartilage and joint fluid. HA lubricates and absorbs shock in the joint. The Food and Drug Administration (FDA) recently approved this therapy for patients with osteoarthritis of the knee if they do not get relief from exercise, physical therapy, or simple analgesics. Numerous clinical investigations have demonstrated the efficacy and safety of injecting of HA in the treatment of osteoarthritis of the knee and other large joints. These clinical studies demonstrated that treatment with HA results in significant improvement in a number of inflammatory and path physiological parameters.

Ginseng, in which the applicable part is the root, contains ginsenosides. Ginsenosides reportedly lower blood pressure; act as an anti-hemolytic, anti-pyretic, anti-psychotic, CNS depressant and ulcer protective activity; and increase GI mobility and decreases islet insulin concentrations. When used orally, ginseng reduces post-pranial blood glucose levels in type 2 diabetics. Ginseng has also been found to lower blood glucose levels and to enhance the efficacy of vitamins C, B and E. Ginseng also acts as an adaptogen, a substance that can act to strengthen the body and increase general resistance.

Vitamin B3, or niacin comes in two forms, nicotinic acid and nicotinamide. The body manufactures niacin by utilizing the amino acid, tryptophan. Nicotinic acid is needed for the proper function of the nervous system and circulatory system. Nicotinamide metabolizes carbohydrates, fats, and proteins. Niacin contributes to more than fifty vital bodily processes. Including the conversion of food into energy, building red blood cells, and synthesizing hormones, fatty acids, and steroids. The body uses vitamin B3 in the process of releasing energy from carbohydrates.

Vitamin C is a water-soluble vitamin that is important in forming collagen, a protein that gives structure to bones, cartilage, muscle, and blood vessels. Vitamin C also helps maintain capillaries, bones, and teeth. IT also aids in the absorption of iron. Vitamin C's crucial importance is in the maintenance of a healthy immune system. Large doses of vitamin C also help relax blood vessels and maintain blood flow.

Vitamin E, also known as tochopherol, is fat soluble and stored in the body in for a short term. The body uses Vitamin E as an anticoagulant and a temperature regulator. Vitamin E appears to play a significant role in boosting the immune system and acts as a powerful antioxidant that protects cell membranes. Vitamin E is essential to the body in order to help improve circulation, promote normal clotting, and allow the muscles to use oxygen.

The present invention is beneficial because it fast absorbing, tasteless, odorless, non-steroidal, and a vasodilator. The invention additive also is a one-time daily large dose. There are no symptoms of nausea, heartburn, constipation, diarrhea, and headaches associates with the present invention. In addition, the present invention contains a high quantity of glucosamine and a high quantity of choindroitin.

The beverage of the present invention is also cost effective since it is capable of being mass-produced. An eight ounce or twelve ounce beverage can contain the single serving daily dose.

The present invention is also beneficial because it perfuses underperufsed tissues. This means the additive saturates the tissue, increases mobility in all directions, decreases inflammation, maintains cartilage viability, increases strength, increases muscle flexibility, and increases endurance.

SUMMARY OF THE INVENTION

The invention is a beverage made of a fluid and a dosage amount in an ingestible amount for treating an inflammatory tissue or arthritic condition in a mammal involving tissue that is underperfused tissue, inflamed joints, or inflamed muscles. The dosage is made of a glucosamine sulfate, glucosamine hydrochloride, and an n-acetyl glucosamine and combinations thereof, chondroitin sulfate, chondroitin hydrochloride and combinations thereof, a member of the family of araliaceae, and a B3 vitamin.

The invention is another beverage made of a fluid and a dosage amount in an ingestible amount for treating an inflammatory tissue or arthritic condition in a mammal involving tissue that is underperfused tissue, inflamed joints or inflamed muscle tissue. The dosage is made of a glucosamine sulfate, glucosamine hydrochloride, and an n-acetyl glucosamine and combinations thereof; a chondroitin sulfate, chondroitin hydrochloride and combinations thereof; a sulfonate with at least one methyl group; and a member of the family of araliaceae.

The invention is also a beverage additive for treating inflammation of the joints and the muscles. The beverage is made of a glucosamine sulfate, glucosamine hydrochloride, and an n-acetyl glucosamine and combinations thereof; a chondroitin sulfate, chondroitin hydrochloride and combinations thereof; a sulfonate with at least one methyl group; and a member of the family of araliaceae.

The invention is also another beverage additive for treating inflammation of the joints and the muscles. The beverage is made of a glucosamine sulfate, glucosamine hydrochloride, and an n-acetyl glucosamine and combinations thereof; a chondroitin sulfate, chondroitin hydrochloride and combinations thereof; a member of the family of araliacea; and a B3 vitamin.

DETAILED DESCRIPTION

Before explaining the present invention in detail, it is to be understood that the invention is not limited to the particular embodiments and that it can be practiced or carried out in various ways.

The invention is a beverage made of a fluid and a dosage amount in an ingestible amount for treating an inflammatory tissue or arthritic condition in a mammal involving tissue that is underperfused tissue, inflamed joints, or inflamed muscle. The dosage amount is made from a glucosamine sulfate, a glucosamine hydrochloride, and an n-acetyl glucosamine and combinations thereof; a chondroitin sulfate, a chondroitin hydrochloride and combinations thereof, a member of the family of araliaceae; and a B3 vitamin. The B3vitamin can be vasodialating niacin, vasodialating nicotinic acid or vasodialating niacinamide.

The invention is another beverage made from a fluid and a dosage amount in an ingestible amount for treating an inflammatory tissue or arthritic condition in a mammal involving tissue that is underperfused tissue, inflamed joints or inflamed muscle tissue. The dosage is a glucosamine sulfate, glucosamine hydrochloride, and an n-acetyl glucosamine and combinations thereof, a chondroitin sulfate, chondroitin hydrochloride and combinations thereof, a sulfonate with at least one methyl group; and a member of the family of araliaceae. The sulfonate with at least one methyl group can be methyl sulfonyl methane (MSM).

In both beverages, the invention contemplates variations in the dosage amounts. The dosage amounts can further include 1000–2000 mg of glucosamine, 500–1500 mg of chondroitin, 250–3000 mg of a sulfonate with at least one methyl group, and 400–800 mg of a member of the family of araliaceae. In addition, the dosage amount can have 500–3000 mg Vitamin C and/or 400–2000 mg Vitamin E.

The araliaceae in the dosage amount can be panax ginseng, Siberian ginseng or American ginseng. Finally, the fluid in the invention's beverages can be water, coffee, tea, artificial drinks, alcoholic fluids, non-alcoholic fluids, fruit juice, vegetable juice, blends of juice, juice and water blends, concentrates of juice, soda, sports drinks or combinations thereof.

The invention is also a beverage additive for treating inflammation of the joints and the muscles. The beverage additive is made of a glucosamine sulfate, glucosamine hydrochloride, and an n-acetyl glucosamine and combinations thereof, a chondroitin sulfate, chondroitin hydrochloride and combinations thereof, a sulfonate with at least one methyl group; and a member of the family of araliaceae. The sulfonate with at least one methyl group can be methyl sulfonyl methane (MSM).

The invention is another beverage additive for treating inflammation of the joints and the muscles. This beverage additive is made of a glucosamine sulfate, glucosamine hydrochloride, and an n-acetyl glucosamine and combinations thereof, a chondroitin sulfate, chondroitin hydrochloride and combinations thereof, a member of the family of araliacea; and a B3 vitamin. The B3 vitamin can be vasodialating niacin, vasodialating nicotinic acid or vasodialating niacinamide.

In both beverage additives, the invention contemplates variations. The beverage additives can further include the lubricating agent sodium hyauluronate. The beverage additives can also include 1000–2000 mg of glucosamine, 500–1500 mg of chondroitin, 10–20 mg of B3 vitamin, and 400–800 mg of a member of the family of araliaceae. The beverage additives can also include 500–3000 mg Vitamin C and/or 400–2000 mg Vitamin E. The araliaceae in the beverage additive can be panax ginseng, Siberian ginseng or American ginseng.

While this invention has been described with emphasis on the preferred embodiments, it should be understood that within the scope of the appended claims, the invention might be practiced other than as specifically described herein.

What is claimed is:

1. A beverage comprising:
   a. a fluid, and
   b. a dosage amount in an ingestible amount for treating an inflammatory tissue in a mammal involving tissue selected from the group comprising underperfused tissue, inflamed joints, and inflamed muscle, wherein said dosage amount comprises:
      i. a glucose ingredient selected from the group consisting of a glucosamine sulfate, a glucosamine hydrochloride, an n-acetyl glucosamine and combinations thereof;
      ii. a chondroitin sulfate, a chondroitin hydrochloride and combinations thereof;
      iii. 400–800 mg of a member of the family of araliaceae for buffering the ingestion of the glucose ingredient; and
      iv. a B3 vitamin.
2. The beverage of claim 1, further comprising a lubricating agent sodium hyaluronate.
3. The beverage of claim 1, wherein the dosage amount comprises
   a. 1000–2000 mg of a glucosamine selected from the group consisting of glucosamine sulfate, glucosamine hydrochloride, n-acetyl glucosamine and combinations thereof;
   b. 500–1500 mg of a chondroitin selected from the group consisting of chondroitin sulfate, chondroitin hydrochloride, and combinations thereof;
   c. 10–20 mg of B3 vitamin.
4. The beverage of claim 1, further comprising 500–3000 mg of Vitamin C.
5. The beverage of claim 1, further comprising 400–2000 mg of Vitamin E.
6. The beverage of claim 1, wherein said member of the family of araliaceae is a ginseng selected from the group: American ginseng, Siberian ginseng, and Panax ginseng.
7. The beverage of claim 1, wherein said B3 vitamin is selected from the group: vasodialating niacin, vasodialating nicotinic acid and vasodialating niacinamide.
8. The beverage of claim 1, wherein the fluid is a member selected from the group consisting of water, coffee, tea, artificial drinks, alcoholic fluids, non-alcoholic fluids, fruit juice, vegetable juice, blends of juice, juice and water blends, concentrates of juice, soda, sports drinks and combinations thereof.
9. A beverage comprising:
   a. a fluid, and
   b. a dosage amount in an ingestible amount for treating an inflammatory tissue in a mammal involving tissue selected from the group comprising underperfused tissue, inflamed joints, and inflamed muscle tissue, wherein said dosage amount comprises:
      i. a glucose ingredient selected from the group consisting of a glucosamine sulfate, a glucosamine hydrochloride, an n-acetyl glucosamine and combinations thereof;
      ii. a chondroitin sulfate, a chondroitin hydrochloride and combinations thereof;
      iii. a sulfonate with at least one methyl group; and
      iv. 400–800 mg of a member of the family of araliaceae for buffering the ingestion of the glucose ingredient.
10. The beverage of claim 9, further comprising the lubricating agent sodium hyaluronate.
11. The beverage of claim 9, wherein the dosage amount comprises
   a. 1000–2000 mg of a glucosamine selected from the group consisting of glucosamine sulfate, glucosamine hydrochloride, n-acetyl glucosamine and combinations thereof;
   b. 500–1500 mg of a chondroitin selected from the group consisting of chondroitin sulfate, chondroitin hydrochloride, and combinations thereof;
   c. 250–3000 mg of a sulfonate with at least one methyl group.
12. The beverage of claim 9, further comprising 500–3000 mg of Vitamin C.
13. The beverage of claim 9, further comprising 400–2000 mg of Vitamin E.
14. The beverage of claim 9, wherein said member of the family of araliaceae is a ginseng selected from the group: American ginseng, Siberian ginseng, and Panax ginseng.
15. The beverage of claim 9, wherein said sulfonate with at least one methyl group is methyl sulfonyl methane (MSM).
16. The beverage of claim 9, wherein the fluid is a member selected from the group consisting of water, coffee, tea, artificial drinks, alcoholic fluids, non-alcoholic fluids, fruit juice, vegetable juice, blends of juice, juice and water blends, concentrates of juice, soda, sports drinks and combinations thereof.
17. A beverage additive for treating inflammation of the joints and the muscles comprising:
   a. a glucose ingredient selected from the group consisting of a glucosamine sulfate, a glucosamine hydrochloride, an n-acetyl glucosamine and combinations thereof;
   b. a chondroitin sulfate, a chondroitin hydrochloride and combinations thereof;

c. a sulfonate with at least one methyl group; and d. 400–800 mg of a member of the family of araliaceae for buffering the ingestion of the glucose ingredient.

18. The beverage additive of claim 17, further comprising the lubricating agent sodium hyaluronate.

19. The beverage additive of claim 17, comprising
   a. 1000–2000 mg of a glucosamine selected from the group consisting of glucosamine sulfate, glucosamine hydrochloride, n-acetyl glucosamine and combinations thereof;
   b. 500–1500 mg of a chondroitin selected from the group consisting of chondroitin sulfate, chondroitin hydrochloride, and combinations thereof,
   c. 250–3000 mg of a sulfonate with at least one methyl group.

20. The beverage additive of claim 17, further comprising 500–3000 mg Vitamin C.

21. The beverage additive of claim 17, further comprising 400–2000 mg Vitamin E.

22. The beverage additive of claim 17, wherein said member of the family of araliaceae is a ginseng selected from the group: American ginseng, Siberian ginseng, and Panax ginseng.

23. The beverage additive of claim 17, wherein said sulfonate with at least one methyl group is methyl sulfonyl methane (MSM).

24. A beverage additive for treating inflammation of the joints and the muscles comprising:
   a. a glucose ingredient selected from the group consisting of a glucosamine sulfate, a glucosamine hydrochloride, an n-acetyl glucosamine and combinations thereof;
   b. a chondroitin sulfate, a chondroitin hydrochloride and combinations thereof;
   c. 400–800 mg of a member of the family of araliaceae for buffering the ingestion of the glucose ingredient; and
   d. a B3 vitamin.

25. The beverage additive of claim 24, further comprising the lubricating agent sodium hyauluronate.

26. The beverage additive of claim 24, comprising
   a. 1000–2000 mg of glucosamine;
   b. 500–1500 mg of chondroitin,
   c. 10–20 mg of B3 vitamin; and
   d. 400–800 mg of a member of the family of araliaceae.

27. The beverage additive of claim 24, further comprising 500–3000 mg Vitamin C.

28. The beverage additive of claim 24, further comprising 400–2000 mg Vitamin E.

29. The beverage additive of claim 24, wherein said member of the family of araliaceae is a ginseng selected from the group: American ginseng, Siberian ginseng, and Panax ginseng.

30. The beverage additive of claim 24, wherein said B3 vitamin is selected from the group: vasodialating niacin, vasodialating nicotinic acid and vasodialating niacinamide.

* * * * *